United States Patent [19]

Vellinga

[11] Patent Number: 5,338,447
[45] Date of Patent: Aug. 16, 1994

[54] BIOREACTOR

[75] Inventor: Sjoerd Vellinga, Tjalleberd, Netherlands

[73] Assignee: Paques B.V., Balk, Netherlands

[21] Appl. No.: 960,359

[22] PCT Filed: Jul. 5, 1991

[86] PCT No.: PCT/NL91/00118

§ 371 Date: Mar. 19, 1993

§ 102(e) Date: Mar. 19, 1993

[87] PCT Pub. No.: WO92/01637

PCT Pub. Date: Feb. 6, 1992

[30] Foreign Application Priority Data

Jul. 19, 1990 [NL] Netherlands ............ 9001654

[51] Int. Cl.⁵ ............................................. C02F 3/28
[52] U.S. Cl. ..................... 210/195.1; 210/202; 210/257.1; 210/261; 210/603; 210/512.1
[58] Field of Search ............ 210/150, 151, 194, 195.1, 210/202, 209, 257.1, 259, 261, 262, 512.1, 603, 615, 616, 821

[56] References Cited

U.S. PATENT DOCUMENTS

| | | | |
|---|---|---|---|
| 2,874,118 | 2/1959 | Albertson | 210/512.1 |
| 3,390,076 | 6/1968 | Dubach | 210/312.1 |
| 4,096,065 | 6/1978 | Brach et al. | 210/512.1 |
| 4,280,902 | 7/1981 | Jacobson et al. | 210/512.1 |
| 4,447,322 | 5/1984 | Zajellik | 210/512.1 |
| 4,663,046 | 5/1987 | Feldkirchner et al. | 210/616 |

FOREIGN PATENT DOCUMENTS

| | | |
|---|---|---|
| 0090450 | 7/1983 | European Pat. Off. |
| 0153299 | 8/1985 | European Pat. Off. |
| 0164508 | 12/1985 | European Pat. Off. |
| 0168283 | 1/1986 | European Pat. Off. |
| 0170332 | 2/1986 | European Pat. Off. |
| 0169620 | 7/1986 | European Pat. Off. |
| 0232853 | 8/1987 | European Pat. Off. |

*Primary Examiner*—Christopher Upton
*Attorney, Agent, or Firm*—Young & Thompson

[57] ABSTRACT

A bioreactor comprising a reactive vessel having an inlet system for material and a reaction chamber located above the inlet system. The inlet system has outflow openings that are at least partially tangentially oriented. A partition separates the reaction chamber from a chamber in which the inlet system is disposed, and the partition has at least one radial slit formed by two radial edge strips overlapping one another and vertically spaced apart. This slit interconnects the chamber in which the inlet system is disposed and the reaction chamber. The partition consists of at least two segments partially overlapping one another. The partition is substantially conical.

9 Claims, 2 Drawing Sheets

BIOREACTOR

The invention relates to a bioreactor comprising a reactor vessel having an inlet system for influent or a mixture of influent and recycled material and a reaction chamber located above this system.

Reactors of this type are used to treat fluids (anaerobically or aerobically), or to prepare substances such as alcohol, with the aid of a biomass.

In the field of anaerobic treatment of waste water, new types of reactors having a high load-taking capacity have been developed in recent years, which reactors are characterised by very high volume loads, a relatively small reaction volume and a slimline high construction. The main types are:
  fluidised bed reactors, in which, for example, sand is present as carrier material or adhesion material for the biomass (see EP-A-0090450)),
  expanded bed reactors, in which an immobilised biomass is present in an expanded bed, and
  internal circulation reactors, in which biogas formed is used to generate circulation of the reactor contents (see EP-A-0170332).

A difficult point with these reactors is the distribution of the influent, which may be mixed with the recycled effluent, over the bottom surface of the reactor. Influent distribution systems are disclosed in EP-B-0090450 (Gist-Brocades), EP-A-0169620 (Paques) and U.S. Pat. No. 4,202,774 (Doff Oliver). In general, a distribution of the influent stream over the reactor bottom such that the sludge bed is subject to a completely stable fluidisation or expansion is not achieved with these systems. The consequence of this is the generation of short-circuit flows and dead corners.

It is known to improve the distribution of the influent by
  using a large number of inlet points uniformly distributed over the reactor bottom, fop example by means of a pipe system, and
  installing a perforated horizontal distributor plate above an inlet point in order to create a pressure drop which leads to a uniform distribution as a result of dissipation of energy.

These inlet systems, which in themselves operate satisfactorily, are subject to a number of disadvantages: If sand or another hard material is present as carrier material, the influent distribution system will undergo enormous wear as a result of the sand blasting effect. If the reactor is temporarily taken out of operation, the sludge bed settles and this causes difficulties in restarting the installation and, moreover, sludge particles can flow back into the distribution system, as a result of which blockages are formed.

The aim of the invention is to overcome these drawbacks and to provide a bioreactor, indicated in the preamble, which produces an excellent distribution of the influent (which may be mixed with recycled material) without there being a risk of blockage and without excessive wear problems arising.

According to the invention, to this end the outflow openings of the influent inlet system are at least partially tangentially oriented and the influent inlet system is located in a chamber which is separated from the reaction chamber by a partition which has at least one radial slit, formed by two radial edge strips vertically overlapping one another some distance apart, which radial slit forms the connection between the said influent inlet chamber and the reaction chamber.

An even better distribution results as a consequence of constructing the partition from two or more segments which partially overlap one another.

Preferably, the partition has an essentially conical shape. An advantage of this is that the material transport from the influent inlet chamber to the reaction chamber also takes place if the inlet chamber is in- completely filled.

It is known per se to use a downcomer to return recycled material to the influent inlet system (see, for example, EP-B-0170332). In this case, the downcomer can also have an outflow opening which is at least partially tangentially oriented.

The said radial slit or slits have n height of between 0.25 and 10 cm, preferably between 0.5 and 3.0 cm. The radial edge strips of the partition overlap one another over a length of 0.5–50 cm, preferably 2.5–25 cm.

Packing pieces can be placed in the slit or slits in order to reduce the passage surface of the slit or slits. The flow rate in the slits will consequently be increased, which leads to a greater pressure drop over the slits and thus to e better distribution.

The invention will now be illustrated in more detail with reference to the figures.

Figure 1:
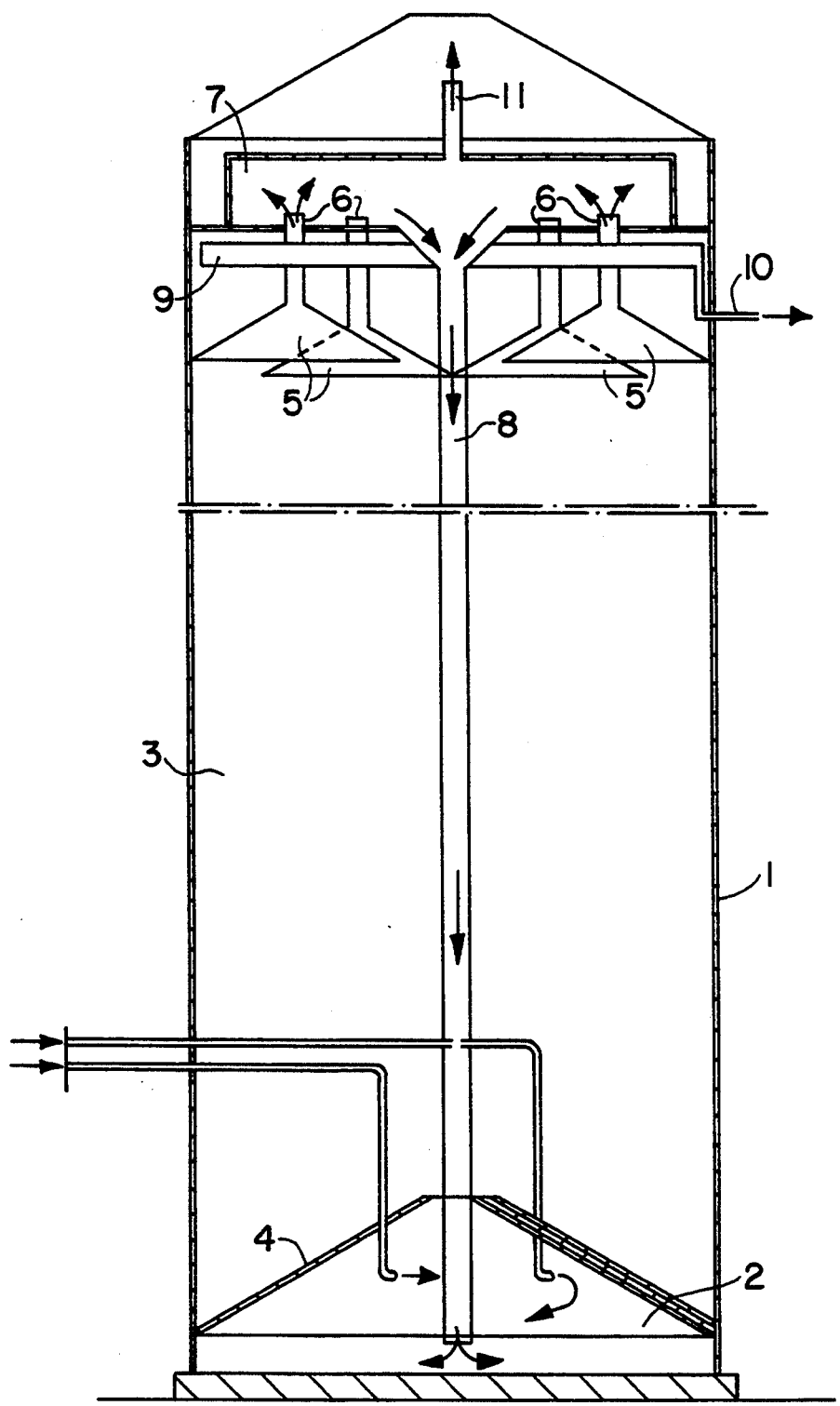
FIG. 1 shows a vertical cross-section of an anaerobic treatment installation having internal circulation.

The reactor shown in FIG. 1 is an anaerobic waste water treatment installation and consists of a vessel 1, in the bottom of which an inlet chamber 2 for influent is located, which inlet chamber is separated from the reaction chamber 3 located above it by a conical wall 4. The influent inlet system which opens into the chamber 2 and which will be described in more detail ensures good distribution of the influent, which flows via openings, which will be described in more detail, in the conical wall towards the reaction chamber.

Under anaerobic conditions, fermentation takes place in the reaction chamber as a result of contact between sludge grains and water-soluble substances, inter alia lower fatty acids, and methane is formed.

In order to produce a steady turbulence-free flow in the uppermost section of the reactor and to ensure that virtually no sludge is discharged with the effluent, a collection system 5, shown diagrammatically, is installed in the reactor, which collection system feeds gas and floatable sludge into risers 6 which open into separation chambers 7, in which fluid and gas are separated from one another. Fluid collects on the bottom of the separation chamber and flows via a downcomer 8 back to the influent inlet chamber 2. Annular effluent gullies 9 having an effluent discharge 10 are located between the collection system 5 and the separation chamber 7. Gas is discharged via a pipe 11.

Figure 2:
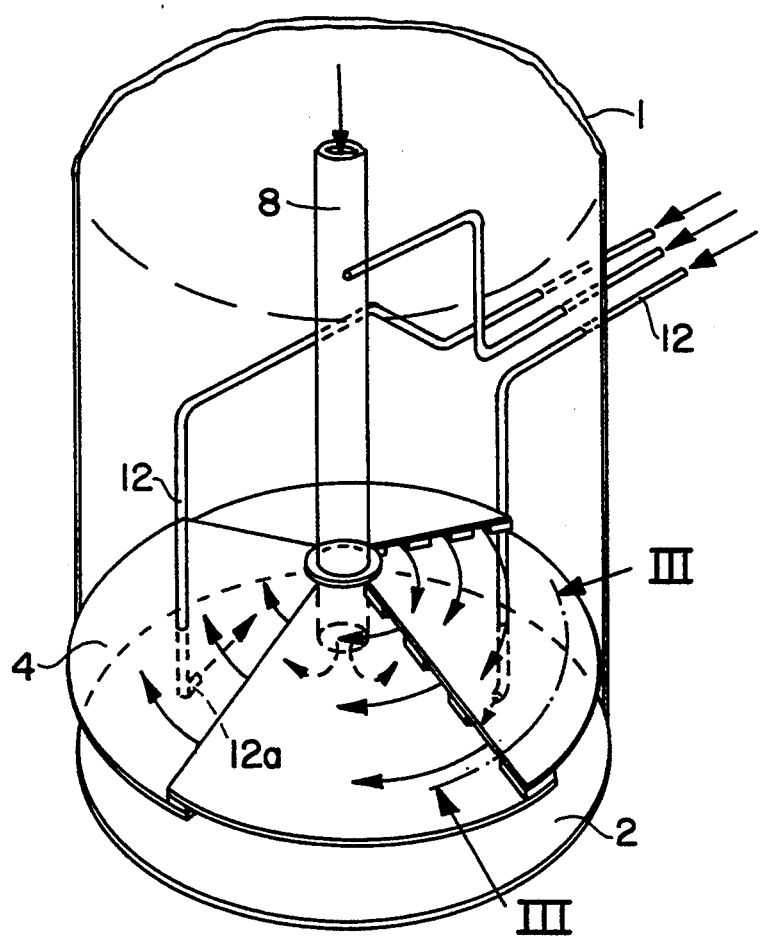
FIG. 2 shows a view of the bottommost section of the reactor according to FIG. 1.
Figure 3:
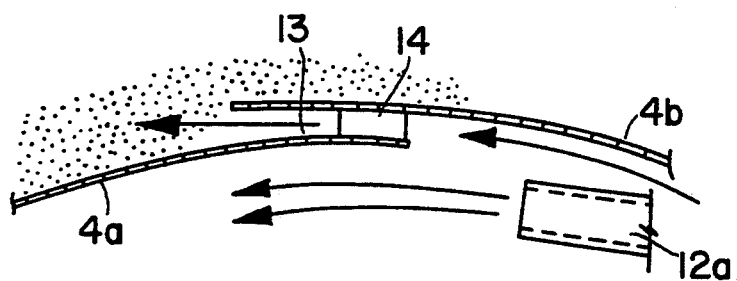
FIG. 3 shows a cross-section of the wall between the influent inlet chamber and the reaction chamber.

The influent inlet pipes are indicated by 12. The outflow ends of these pipes are tangentially positioned, as a result of which a rotary eddying motion directed in the direction of the arrows in FIG. 2 is imparted to the fluid present in the inlet chamber 2. As a result of this rotary motion, complete mixing takes place. The outlet of the downcomer 8 can also be oriented tangentially to support the rotation.

The conical wall 4 consists of a number of segments 4a, 4b and so on, which overlap one another some vertical distance apart in order to form radial slits 13. These form the connection between the chamber 2 and the reaction chamber. The feed from the chamber 2 into the reaction chamber 3 is uniformly distributed over all free slit sections.

If the feed to the reactor is stopped, the biosludge will settle in the reaction chamber 3 (where appropriate with carrier material) on the conical wall 4 and, as a consequence of the overlaps of the segments, the settled sludge is unable or barely able to flow back into the chamber 2. This back-flow is also prevented by the packing pieces 14. Blockage is consequently virtually impossible.

When the reactor is taken into service again, complete mixing of the contents of the chamber 2 is achieved again within a short time. This complete mixing and the exclusion of blockage are the most important advantages of the construction described.

FIG. 2 indicates that one of the influent inlet pipes 12 opens into the downcomer. This can be advantageous, but is not necessary. The invention is not restricted to an anaerobic waste water treatment installation, but can also be used on aerobic reactors. The biomass can be immobilised, for example, on an inert carrier material.

The height of the radial slit or slits is between 0.25 and 10 cm, preferably between 0.5 and 3.0 cm, while the radial edge strips of the segments overlap one another over a length of 0.5–50 cm, preferably 2.5–25 cm.

I claim:

1. A bioreactor comprising a reactive vessel having an inlet system for material and a reaction chamber located above said inlet system, said inlet system having outflow openings that are at least partially tangentially oriented, the bioreactor comprising a partition that separates the reaction chamber from a chamber in which said inlet system is disposed, said partition having at least one radial slit formed by two radial edge strips overlapping one another and vertically spaced apart, said at least one radial slit interconnecting said chamber in which said inlet system is disposed and said reaction chamber.

2. A bioreactor as claimed in claim 1, wherein the partition consists of at least two segments partially overlapping one another.

3. A bioreactor as claimed in claim 1, wherein the partition is substantially conical.

4. A bioreactor as claimed in claim 1, including at least one downcomer for returning material recycled to said inlet system, said downcomer having an at least partially tangentially oriented outflow opening.

5. A bioreactor as claimed in claim 1, wherein said at least one radial slit has a length between 0.25 and 10 cm.

6. A bioreactor as claimed in claim 5, wherein said length is between 0.5 and 3.0 cm.

7. A bioreactor as claimed in claim 1, wherein said radial edge strips overlap one another over a length of 0.5 to 50 cm.

8. A bioreactor as claimed in claim 7, wherein said length is 2.5 to 25 cm.

9. A bioreactor as claimed in claim 1, further comprising packing pieces disposed in said at least one slit to reduce the passage area of said at least one slit.

* * * * *